(12) United States Patent
Kawashima (10) Patent No.: US 7,332,727 B2
(45) Date of Patent: Feb. 19, 2008

(54) METHOD AND DEVICE FOR GENERATING ULTRA-HIGH PRESSURE

(75) Inventor: Yasushi Kawashima, Tokyo (JP)

(73) Assignee: Tokai University Educational System, Tokyo (JP)

( * ) Notice: Subject to any disclaimer, the term of this patent is extended or adjusted under 35 U.S.C. 154(b) by 579 days.

(21) Appl. No.: 10/284,477

(22) Filed: Oct. 31, 2002

(65) Prior Publication Data

US 2003/0089861 A1    May 15, 2003

(30) Foreign Application Priority Data

Oct. 31, 2001   (JP) .............................. 2001-335271

(51) Int. Cl.
*B29C 43/00* (2006.01)
(52) U.S. Cl. .............................. 250/458.1; 73/864.91; 425/77
(58) Field of Classification Search ............. 250/458.1; 73/864.91; 425/77
See application file for complete search history.

(56) References Cited

U.S. PATENT DOCUMENTS 4,776,223 A * 10/1988 Moss ...................... 73/864.91
5,360,477 A * 11/1994 Inoue et al. .................... 117/4
5,693,345 A * 12/1997 Chen et al. ..................... 425/77
6,543,295 B2 * 4/2003 Xu et al. ....................... 73/818

OTHER PUBLICATIONS

Kanda et al., "The Properties of Zirconia Pressure Medium Prepared By Powder Compaction with a Sodium Silicate Solution" 1987, abstract.*

* cited by examiner

*Primary Examiner*—David Porta
*Assistant Examiner*—Christine Sung
(74) *Attorney, Agent, or Firm*—Birch, Stewart, Kolasch & Birch, LLP (57) ABSTRACT

A pressure source material is loaded into a space having constraint device 1, which is formed partly by optically transparent material 1*a*, 1*b*, and is disrupted under volume constraint. Light energy is externally supplied to the pressure source material constrained in the space through the optically transparent material by employing the device to apply light energy. The disruption of atomic bonds in the pressure source material is induced by heating through the supplied energy. Exceptionally high pressures are generated in the space by the use of expansive forces arising from the disruption of atomic bonds. Such a configuration can implement ultrahigh pressure abilities that has not been achieved, so far.

15 Claims, 5 Drawing Sheets

METHOD AND DEVICE FOR GENERATING ULTRA-HIGH PRESSURE

BACKGROUND OF THE INVENTION

1. Field of the Invention

The present invention relates to a method and device for generating ultrahigh-pressure, and more particularly to a method and device which enables the generation of ultrahigh pressure in a space partly surrounded by a optically transparent material with supplying light energy to the space externally.

2. Description of the Related Art

Although belt apparatus, multi-anvil apparatus and so on which enable the syntheses of diamond and cubic boron nitride have generally been used for the production of high pressure, high pressures above 10 GPa is difficult to achieve by using these apparatuses. The apparatuses can produce static high pressures and the sample volume can be enlarged up to 200 cm$^3$. However, it is quite impossible to achieve high pressures in excess of 100 GPa in these apparatuses. High pressures in the 100-GPa region can be attained only with diamond anvil cells or dynamic methods.

However, the sample volume attainable in diamond anvil cells is not much larger than 10$^{-9}$ cm$^3$ at pressures above 100 GPa. Large-scale apparatuses are needed for ultrahigh pressure experiments using high explosives or gas guns which have generally been used in dynamic methods. The shock duration is extremely short and limited to a few microseconds. Furthermore, it has not been reported until now that ultrahigh pressures above 1 TPa are generated by these dynamic methods. The generation of ultrahigh pressure beyond 1TPa has been achieved only in impact experiments using nuclear explosion or high-power lasers developed for the purpose of nuclear fusion. However, the duration of generated ultrahigh pressure cannot exceed a few nanoseconds.

Since the sample volume of diamond anvil cells is extremely small, the diamond anvil cell is impossible to use in industrial production. Furthermore, the production of ultrahigh pressures in excess of 1 TPa using diamond-cell technique cannot be expected. In the conventional dynamic methods, the duration of the high-pressure generation is extremely short. The applications of the dynamic methods to syntheses of materials via phase transformation are limited to irreversibly formed metastable phases. Thus, the conventional dynamic methods have application only in the extremely limited region.

SUMMARY OF THE INVENTION

In view of the above-described impasse, a main object of the invention is to provide a method and device for generating ultra-high pressure that have not been achieved in the conventional methods, so far.

Another object of the invention is to provide a method and device for generating ultra-high pressure with considerably longer duration compared to the conventional dynamic methods.

Still another object of the invention is to provide a method and device for generating ultra-high pressure in extremely larger sample chamber compared to the diamond anvil cells.

Yet another object of the invention is to provide a method and device for generating ultra-high pressure with the supply of energy some orders of magnitudes less than those in the conventional dynamic methods.

A further object of the invention is to provide a method and device for generating ultra-high pressure in which high temperature and high pressure required for syntheses can be simultaneously produced in the sample chamber and the high temperature can be controlled separately.

In accordance with the present invention, there is provided a method for generating ultra-high pressure comprising the steps of:

loading a pressure source material under volume constraint in a space partly surrounded by an optically transparent material, the ultra-high pressure source material being expanded in volume through disruption of its atomic bonds;

disrupting the atomic bonds by heating the pressure source material using optical energy externally supplied to the pressure source material through the optically transparent material; and generating ultra-high pressure within the space using expansive force of the high pressure inducing material arising from the disruption of atomic bonds.

In the method described above, a pressure source material expanded due to the breaking of its atomic bonds is packed in a space partly surrounded by optically transparent material and light energy is externally supplied to the pressure source material through the optically transparent material to disrupt its atomic bonds by heating under volume constraint. Therefore, since ultrahigh pressures are generated by expansive forces arising from the disruption of atomic bonds in the pressure source material, if only a relatively small light energy enough to induce the disruption of atomic bonds is supplied to the pressure source material, ultrahigh pressures can be generated. Furthermore, pressures generated in the volume-constrained space are exceptionally high because expansive forces occurring from the pressure source material disrupted against its very strong bonding forces are extremely large.

In a preferred embodiment, the pressure source material is irradiated with pulsed laser light through the optically transparent material to supply the light energy.

Since the supply of light energy is made by the irradiation of pulsed laser light through the optically transparent material, the light energy can be efficiently supplied to the pressure source material and well controlled by changing the intensity and the duration of pulsed laser from the existing pulsed laser equipment which can emit laser lights having a wavelength suitable for heating the pressure source material.

In a preferred embodiment, the optically transparent material is high transmittance to the pulsed laser light.

Since the optically transparent material has high transmittance for the pulse laser light, the externally supplied light energy can pass the optically transparent material without raising its temperature due to energy absorption and thermal stresses causing damage to the optically transparent material can hardly occur.

In a preferred embodiment, the optically transparent material is sapphire.

Since sapphire has high transmittance compared with diamond and a large single crystal of synthetic sapphire is available at a low price, it is suitable for the optically transparent material forming the space in which high pressures are generated.

In a preferred embodiment, the pressure source material is made of a simple substance having a large absorption coefficient and strong atomic bonds, or a compound substance which is a mixture of materials having the large absorption coefficient and/or the strong atomic bonds to provide the large absorption coefficient and strong atomic bonds as a whole.

Since the pressure source material is a substance having large absorption coefficient and strong atomic bonds, considerably large expansive forces can occur if only a relatively small energy is supplied to the pressure source material. Furthermore, since the pressure source material is a mixture of materials, which has large adsorption coefficient or strong bonds, possessing large absorption coefficient and strong atomic bonds as a whole, the generated pressure and its duration can be controlled by combining materials.

In a preferred embodiment, the type of the atomic bonds is a covalent bond, a metallic bond or a hydrogen bond.

The pressure source material can be chosen among materials which have covalent, metallic, and hydrogen bonds according to need. Therefore, temperature of the pressurized and heated sample can be controlled because temperature gradients across the pressure source material can be changed by combining materials that have different light absorption coefficients or various types of atomic bonds.

In a preferred embodiment, the simple substance is graphite.

Since graphite has not only large light absorption coefficient but also strong covalent bonds, graphite can be singly used as the pressure source material and furthermore the use of graphite as pressure source material enables the generation of ultrahigh pressure with high energy efficiency.

In a preferred embodiment, the compound substance is a mixture of powdered graphite and water.

Since hydrogen bonds or atomic bonds in water are disrupted by heat occurring in graphite which absorbs light energy, large expansion of water takes place. Therefore, the maximum pressure generated in the mixture of graphite and water can be higher than that in individual graphite.

In a preferred embodiment, the pressure source material is irradiated with a pulsed laser beam through the optically transparent material in such a manner that the pulsed laser beam has a beam spot having a diameter adjusted to that of the pressure source material so that the pulsed laser light. provides a minimum diameter not within the optically transparent material.

The pulsed laser beam is condensed on the pressure source material through the optically transparent material so that the minimum diameter of the laser beam is not formed within the optically transparent material. Therefore, as the position where the intensity of pulsed laser beam is highest does not exist in the inside of the optically transparent material, the local temperature increase in the optically transparent material can be avoided.

In accordance with this invention, there is provided a a method for generating ultra-high pressure comprising the steps of:

loading at least graphite as a pressure source material under volume constraint in a space surrounded by optically transparent sapphire anvils;

disrupting the atomic bonds of the graphite by irradiating the graphite under volume constraint with pulsed laser light externally through the sapphire anvils; and generating ultra-high pressure within the space using force arising from the disruption of atomic bonds.

Since graphite is at least loaded under volume constraint into a space partly surrounded by optically transparent material and the graphite is disrupted by light energy supplied externally through the optically transparent material and thereby ultrahigh pressures are generated in the space by the use of expansive forces arising from the disruption of covalent bonds in graphite, the supplied light energy is efficiently absorbed in the graphite, which is quickly heated up to a high temperature required to disrupt the atomic covalent bonds in graphite and exceptionally high pressure can accordingly be achieved with a relatively small light energy because very large expansive forces occur in the graphite disrupted against its very strong covalent bonds.

In accordance with the invention, there is provided a device for generating ultra-high pressure comprising:

loading means for loading a pressure source material under volume constraint in a space partly surrounded by an optically transparent material, the ultra-high pressure source material being expanded in volume through disruption of its atomic bonds; and light energy supplying means for externally supplying optical energy to the pressure source material through the optically transparent material, wherein the pressure source material is heated by the light energy externally supplied by the light energy supplying means so that the atomic bonds are disrupted, and ultra-high pressure is generated within the space using expansive force of the high pressure inducing material arising from the disruption of atomic bonds.

In the device described just above, a pressure source material is packed under volume constraint in a space partly surrounded by optically transparent material which is equipped with the device to constrain expansion. By means of the device to supply light energy, light energy is externally supplied to the pressure source material under volume constraint through optically transparent material to disrupt its atomic bonds by heating and ultrahigh pressures are generated in the space by expansive forces arising from the disruption of atomic bonds in the pressure source material. Therefore, ultrahigh pressures can be generated by a relatively small light energy enough to induce the disruption of atomic bonds by heating. Furthermore, pressures generated in the volume-constrained space are exceptionally high because expansive forces occurring from the pressure source material disrupted against its very strong bonding forces are extremely large.

In a preferred embodiment of the device, the means for supplying light energy is equipped with a pulse laser that emits a pulsing laser beam applied to the pressure source material through the optically transparent material.

In this configuration, light energy can be efficiently supplied to the pressure source material through the optically transparent material by controlling the intensity and the duration of the pulsing laser using the existing pulsing laser equipment that can emit laser beam having a suitable wavelength for heating the pressure source material.

In a preferred embodiment of the device, the light energy supplying means has an optical adjusting system for adjusting the diameter of the laser beam so that the pulsing laser beam provides a minimum diameter not within the optically transparent material before the pulsing laser beam penetrates the optically transparent material. Since by using the device to supply light energy to the pressure source material, the pulsing laser beam can be condensed on the pressure source material through the optically transparent material so that the minimum diameter of the laser beam is not formed within the laser-irradiated optically transparent material and the spot diameter at the pressure source material can be determined, the position where the intensity of pulsing laser beam is highest, does not exist in the inside of the optically transparent material and thereby the local temperature increase in the optically transparent material can be avoided.

In a preferred embodiment of the device, the light energy supplying means has an optical splitting means for splitting the pulsed laser beam into plural parts to be applied to the high pressure source material constrained in the space from plural directions.

In this configuration, the laser beam is divided into some ones and the divided laser beams are separately applied to the pressure source material constrained in the space from some different directions. Therefore, as larger expansion occurs in the space compared to the case of irradiating in one direction, higher pressure can be achieved.

In an preferred embodiment of the device, a radiative transition material is loaded together with the high pressure source material in the space, the radiative transition material emitting fluorescence excited by laser and changing its wavelength according to pressure within the space, and the device further comprises:

a wavelength measuring means for measuring the wavelength of the fluorescence emitted by the radiative transition material; and a pressure estimating means for estimating the ultra-high pressure generated within the space from shifts in wavelength of the fluorescence emitted from the radiative transition material.

Since the pressure sensor which changes the wavelength of fluorescence emission dependently on pressure is loaded into the space together with the pressure source material, high pressures generated in the space can be measured on the basis of the observed wavelength of the fluorescence from the pressure sensor using the optical system. Therefore, how the generated pressure changes by the use of various pressure source materials or by the way of supplying light energy, can be investigated.

In a preferred embodiment, the device further comprises: means for measuring the temperatures of the space, wherein spectra of thermal radiations from the space are observed during disruption of the pressure source material and the temperatures are obtained from the observed spectra.

Since spectra of thermal radiations from the space during the disruption of the pressure source material can be observed and temperatures in the space can be estimated from the observed spectra, how the temperature of the space changes during the disruption of atomic bonds by the use of various pressure source materials or by the way of supplying light energy, can be investigated.

The above and other objects and features of the invention will be more apparent from the following description taken in conjunction with the accompanying drawings.

DESCRIPTION OF THE PREFERRED EMBODIMENTS

Figure 1:
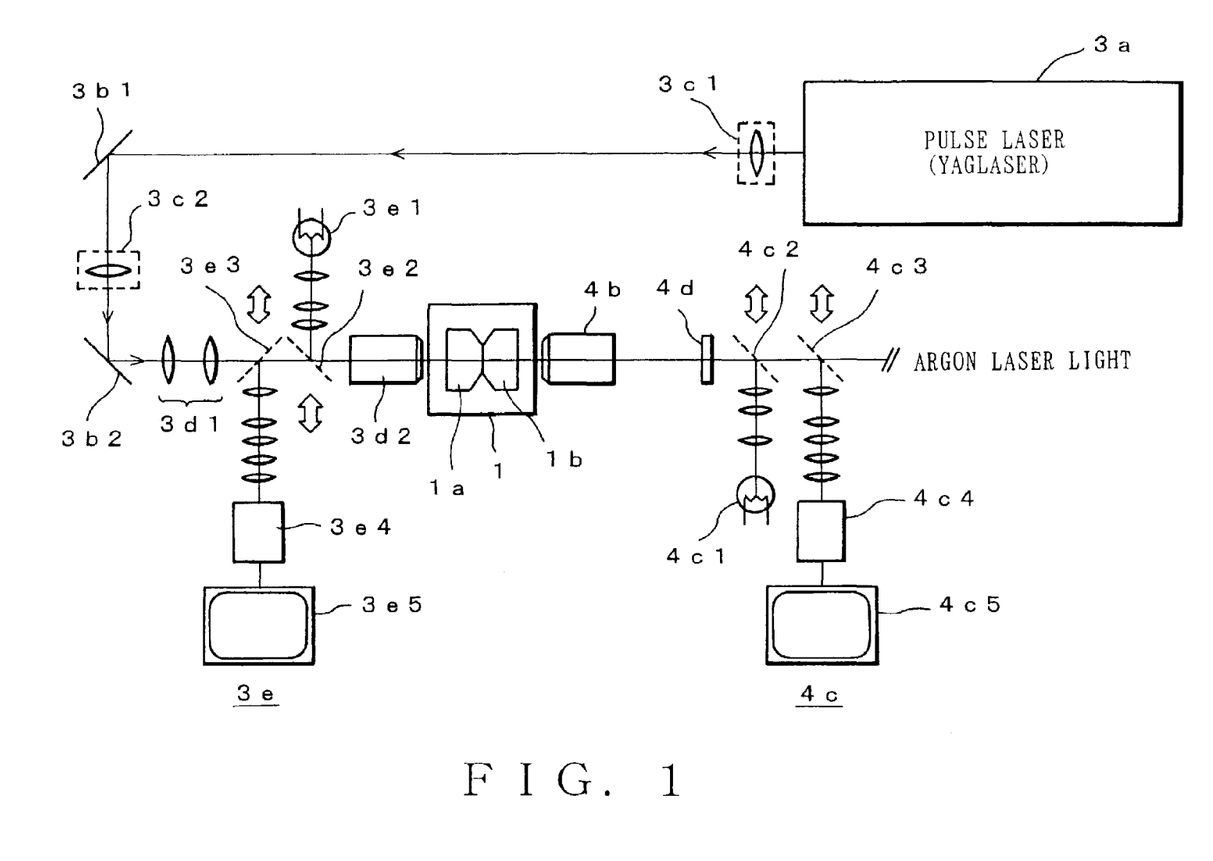
FIG. 1 is a schematic view showing an embodiment of a ultra-high pressure device generating ultrahigh pressures employing the ultra-high pressure method based on the present invention.
Figure 2:
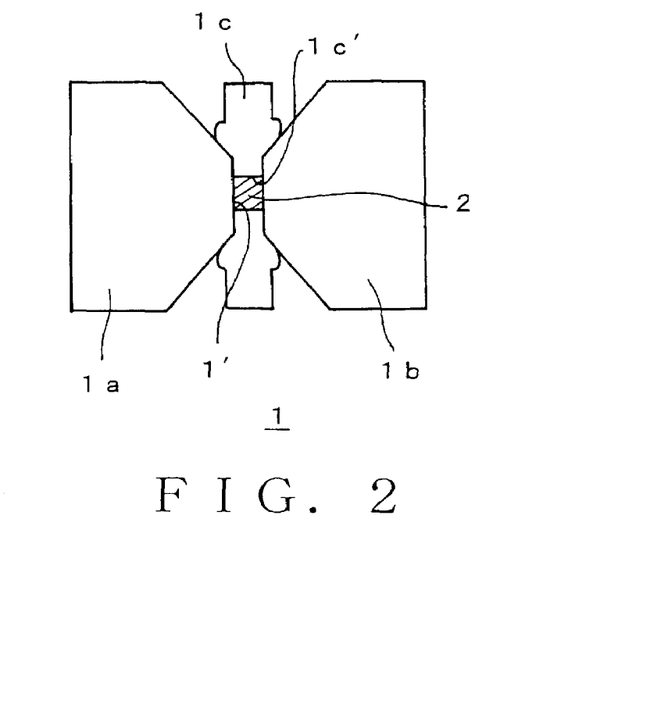
FIG. 2 is a sectional side view showing the high-pressure device 1 in FIG. 1.

Referring to the accompanied drawings showing an embodiment of the invention, the present invention will be explained FIG. 1 is a schematic drawing showing an embodiment of the device based on the ultra-high pressure method according to the present invention. In FIG. 1, the ultra-high pressure device has a space partly surrounded by optically transparent material where a pressure source material is loaded and its atomic bonds are disrupted under volume constraint, and in which a high-pressure device 1 to constrain expansion of the pressure source material is installed. The high-pressure device 1 will be explained in detail referring to FIG. 2. As shown in FIG.2, the high-pressure device consists of a pair of sapphire anvils 1a, 1b having high transmittance and gasket 1c having a hole which form a space 1' where the pressure source material 2 is loaded, and a screw-clamped anvil cell (not illustrated) which holds the sapphire anvils and presses the gasket 1c between the flat parallel faces of the sapphire anvils.

The gasket 1c illustrated in FIG. 2 is held between the pressure faces of a pair of sapphire anvils so that the pressure source material is compressed to 5 GPa. As shown in FIG. 2, a part of the gasket 1c sandwiched between the sapphire anvils is crushed and the circumferential region of this part rises. The gasket shown as an example was Cu—Be foil of 0.2 mm thickness with a hole (0.15 mm in diameter) before compressing it by sapphire anvil cell. The volume of the space 1' is $3.53 \times 10^{-3}$ mm$^3$. A foil of soft metal such as Cu—Be or Cu is usually used as gasket for sapphire anvil because such soft metal does not damage the pressure face of sapphire anvil.

The ultra-high pressure apparatus is equipped with a device to apply light energy which generates light energy to externally supply light energy to the pressure source material constrained in the space 1' of the high-pressure device 1 through a pair of sapphire anvils 1a, 1b. The device has a pulsed laser equipment 3a that generates pulsed laser light supplied to the pressure source material through a pair of sapphire anvils 1a, 1b. For example YAG laser is used as the pulsed laser 3a. In this embodiment, the pulsed YAG laser using slab type Nd:YAG crystal was chosen, which can generate high power laser with a good beam quality. In this pulsed laser equipment, the peak power and the duration of pulsed laser can be changed arbitrarily.

The device to apply light energy has two mirrors 3b1, 3b2 which reverse the direction of laser light from pulsed laser 3a. A laser light from the pulsed laser 3a is reflected from mirror 3b1 so that it changes its direction at right angles, and the laser light reflected from mirror 3b1 changes its direction at right by mirror 3b2 again.

Owing to the use of slab type Nd:YAG crystal, the spot of laser beam from the pulsed laser 3a has a rectangular shape and the rectangular spot becomes to be elongated as the position is apart from an exit of the pulsed laser 3a because of difference in spreading between width and length. In order to prevent the beam expansion and the elongation of beam spot, a circular aperture is placed in the resonator of the pulsed laser 3a and furthermore pupil transfer lens 3c1 and 3c2 are put between pulsed laser 3a and mirror 3b1 and between pulsed laser 3a and mirror 3b2, respectively. Thus, in order to use the output power of the pulsed laser effectively, said device is devised to obtain beam spot as circular as possible. By means of the device to apply light energy, laser light from mirror 3b1 is reflected by mirror 3b2 and the reflected laser light is applied to the pressure source material constrained in the space of the high-pressure device 1 through sapphire anvil 1a and the size of the beam spot at the pressure source material is adjusted so that the minimum diameter of the laser beam is not formed within sapphire anvil 1a. The size of the laser spot is determined by changing the positions of lens 3d1 after adjusting the focus of objective lens 3d2. The position and the size of beam spot are decided using monitor system 3e. When the position and the size of beam spot are adjusted observing the pulsed laser spot, a dimming filter (not illustrated) is put in laser light paths.

After the focus of objective lens 3d2 is adjusted to the interface between sapphire anvil 1a and pressure source material 2, the positions of lens 3d1 are controlled so that the size of laser beam spot at the interface between sapphire anvil 1a and pressure source material 2 coincides with that of the end of pressure source material 2.

In the monitor system 3e, lights from a source of illumination 3e1 are reflected by beam splitter 3e2 and the reflected lights are applied to the interface between sapphire anvil 1a and pressure source material 2 through objective lens 3d2. The interface is taken with CCD camera 3e4 through. objective lens 3d2 and beam splitter 3e2, 3e3, which is projected on the monitor 3e5. The focus of objective lens 3d2 is adjusted to the interface while observing the picture of the interface projected on the monitor 3e5 so that a clear picture can be projected.

As described above, the size of laser spot at the interface approximately agrees with that of the end of pressure source material 2 when the objective lens 3d2 is focused. When a trial pulsed laser light of low intensity emitted from pulsed laser 3a is applied to the pressure source material 2 through the dimming filter, the spot of the laser light at the interface can be observed by monitor 3e5. Thereby it can be confirmed whether the size of laser spot at the interface approximately agrees with that of the end of pressure source material 2 or not. After that, beam splitters 3e2 and 3e3 in the monitor system 3e are removed from the laser light paths as indicated by arrows in FIG. 1.

As described above, after the position and the size of beam spot are decided using monitor 3e, beam splitters 3e2 and 3e3 in the monitor system 3e are removed from the laser light paths and subsequently a laser beam having the predetermined energy and duration is emitted from the pulsed laser 3a. The pressure source material 2 which is loaded under volume constraint in the space 1', is irradiated with the laser beam through pupil transfer lens 3c1, mirror 3b1, pupil transfer lens 3c2, mirror 3b2, lens 3d1, objective lens 3d2, and sapphire anvil 1a. The pressure source material 2 is heated with the irradiation of the pulsed laser, which is disrupted by heating and expanded due to the disruption. Since the expansive forces arising from the disruption of atomic bonds are very large, ultrahigh pressures are generated in the space 1'.

The ultra-high pressure device shown in FIG. 1 is also equipped with a pressure-measurement system for measuring ultrahigh pressures generated in the space 1' and a temperature-measurement system for observing temperatures in the space 1' based on thermal radiations from the space 1' during the disruption of the pressure source material. Before the explanation of the pressure and temperature measurement systems, the principles of the present pressure and temperature measurements will be explained referring to FIG. 3.

Figure 3:
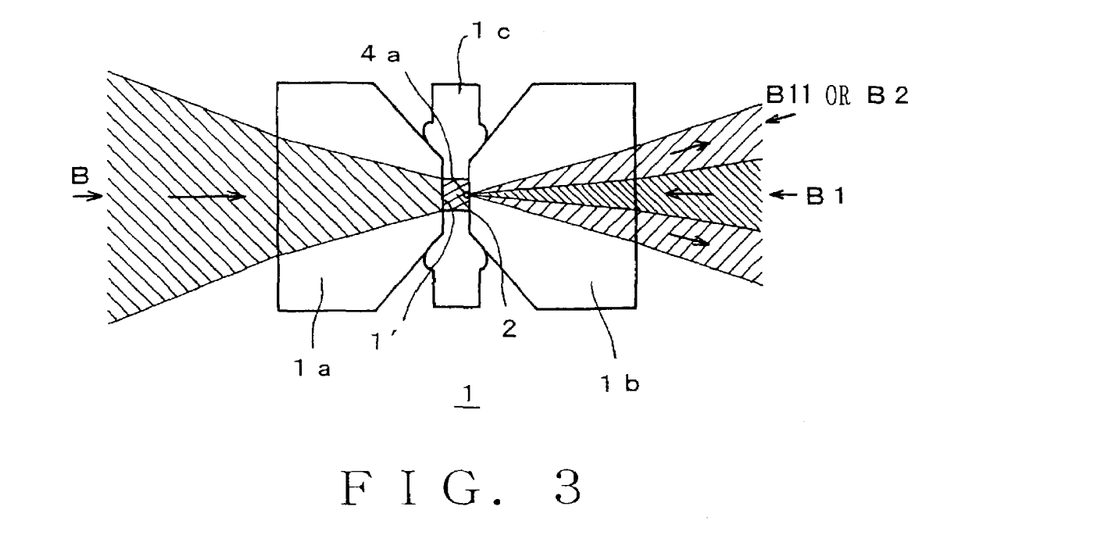
FIG. 3 is a diagram illustrating the methods to measure ultrahigh pressure and ultrahigh temperature generated by the use of the present invention.

As shown in FIG. 3, a ruby 4a used as pressure sensor is loaded in the place 1' together with the pressure source material 2 so that it is placed near the interface between the pressure source material 2 and the sapphire anvil 1b opposite to the sapphire anvil 1a through which pulsed laser beam B passes. The pressure source material is disrupted by heating through the irradiation of pulsed laser. The expansive forces resulting from the disruption is transmitted in the pressure source material 2 packed in the space 1' and is exerted on the ruby 4a, in which ultrahigh pressures are generated.

Fluorescence emission (B11) from the ruby 4a is excited by the irradiation of laser beams B1 through sapphire anvil 1b. Since the wavelength of the fluorescence depends on pressure exerted on the ruby 4a in the space 1', ultrahigh pressure generated in the space 1' can be estimated by measuring the wavelength of fluorescence B11 from the ruby 4a.

When the ruby is not irradiated with the excitation laser beam B1 through sapphire anvil 1b, spectra of thermal radiations emitted through the sapphire anvil 1b from the space 1' are observed at the interface between sapphire anvil 1b and pressure source material 2. In order to eliminate influences of the optical system which the radiant lights pass, a spectrum of radiation from the standard light source is measured by using the optical system. The spectra of thermal radiation from the space 1' are corrected on the basis of this result. Thus temperatures at the interface in the space 1' can be measured.

Returning to FIG. 1, an explanation of the pressure and temperature measurement systems follows. The objective lens 4b to irradiate the ruby 4a with excitation laser beam B1 and the monitor system 4c to adjust the focus of the objective lens 4b are installed in the system.

The monitor system 4c has the same configuration as the monitor system 3e. In the monitor system 4c, lights from the illumination-light source are reflected by beam splitter 4c2, the reflected lights are applied to the interface between sapphire anvil 1b and pressure source material 2 through objective lens 4b. The interface is taken with CCD camera 4c4 through objective lens 4b and beam splitter 4c2, 4c3, which is projected on the monitor 4c5. The focus of objective lens 4b is adjusted to the interface while observing the picture of the interface projected on the monitor 4c5 so that a clear picture can be projected on the monitor 4c5.

After the focus of objective lens 4b is adjusted to the interface, beam splitters 4c2 and 4c3 in the monitor system 4c are removed from the laser light paths as indicated by arrows in FIG. 1. At the pressure measurement, beam splitters 4c2 and 4c3 in the monitor system 4c are removed from the laser light paths. The laser beams from the argon laser to excite fluorescence emissions form ruby are reflected by beam splitter (not illustrated) and the reflected laser beams are applied to the ruby 4a in the space 1' through objective lens 4b so that the ruby 4a emits the fluorescence B11. The fluorescence from the ruby 4a passes beam splitter (not illustrated) and reaches the monochromator (not illustrated) where the ruby fluorescence lights are dispersed.

At the temperature measurement, radiant lights from the interface between the sapphire anvil 1b and the sample are made parallel by objective lens 4*b* and are transmitted to the monochromator (not illustrated). The observed spectra of radiation from the space 1' are corrected. The temperatures at the interface in the space where ultrahigh pressure is generated, are obtained on the basis of the corrected spectra. Here, 4*d* is a notch filter for YAG-laser wavelength which cut off only the YAG laser light so that the pulsed laser light could not reach the optical system for measuring temperature and pressure to damage it.

Figure 4:
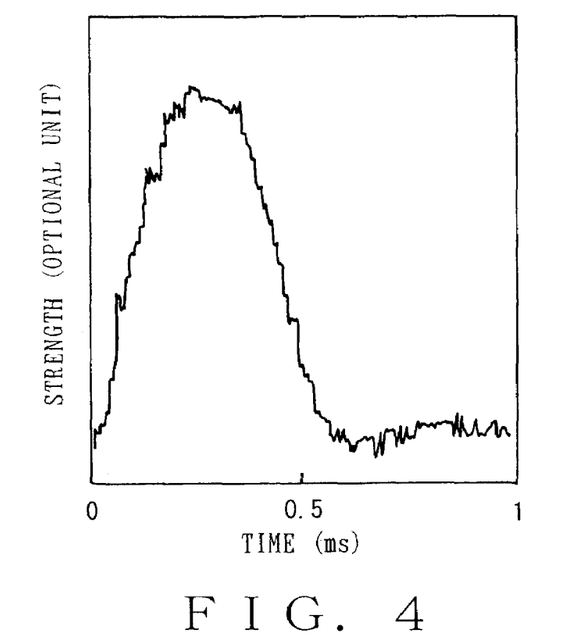
FIG. 4 is a graph showing the form of pulsed laser emitted from the pulsed laser equipment in FIG. 1.
Figure 5A:
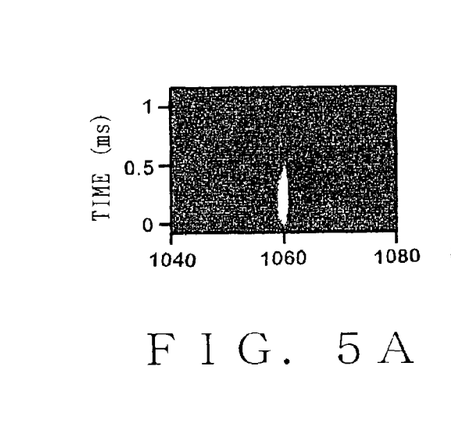
FIGS. 5A and 5B are CCD camera records of pulsed laser applied to the pressure source material and the pressure shifts of ruby fluorescence lines, which were measured during the ultrahigh pressure experiment in which graphite is used as pressure source material.
Figure 5B:
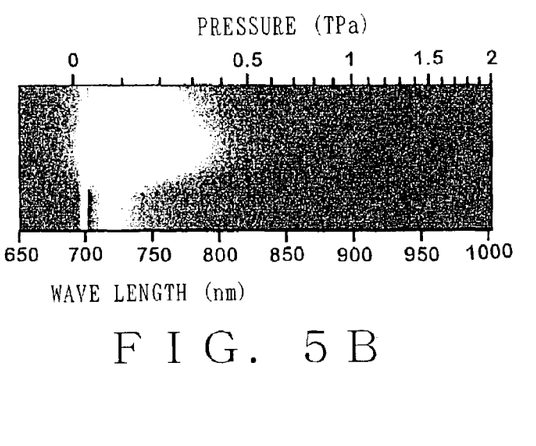

By the use of the ultra-high pressure apparatus described above, powdered graphite is loaded into the space 1', which is formed by a pair of sapphire anvils 1*a*, 1*b*, and gasket 1*c*, together with ruby 4*a* under volume constraint. As shown in FIG. 4, the powdered graphite is heated with the irradiation of 0.5 ms-duration pulsed laser having a wavelength of 1060 nm emitted from the YAG pulse laser equipment through one sapphire anvil 1*a*. The atomic covalent bonds in graphite are disrupted by heating. Then fluorescence emission from the ruby 4*a* was dispersed by the monochromator and the change in wavelength of the fluorescence was recorded in a cooled CCD camera. The recorded time-resolved ruby fluorescence is shown in FIG. 5(*b*). As seen from the pressure scale which is estimated from the wavelength scale, ultrahigh pressures in the 400-500 GPa region are achieved in the space 1' of the high pressure device 1 with the duration of about 0.5 ms because of the disruption of atomic covalent bonds in graphite. The amount of energy supplied to the pressure source material by pulse laser equipment 3*a* is estimated to be 0.25 J, which is converted into the energy per unit area and unit time of $3.5 \times 10^6$ W/cm$^2$. FIG. 5(*a*) shows the wavelength and the duration of pulsed laser. The pressure scale in FIG. 5(*b*) is obtained based on the well known relation between pressure p [TPa] and the shift Δλ [nm] in the wavelength of $R_1$ ruby fluorescence:

$$p=0.3808[(\Delta\lambda/694.2+1)^5-1].$$

Figure 6A:
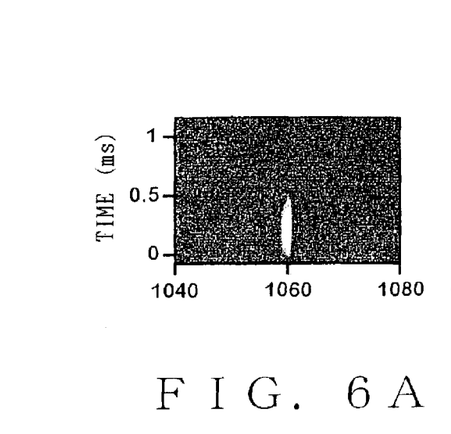
FIGS. 6A and 6B are CCD camera records of pulsed laser applied to the pressure source material and the pressure shifts of ruby fluorescence lines, which were measured during the ultrahigh pressure experiment where a mixture of powdered graphite and water is used as the pressure source material.
Figure 6B:
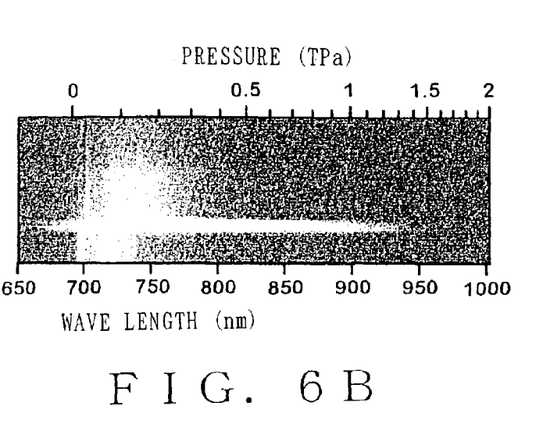

A small quantity of water was dropped into powdered graphite and this mixture of powdered graphite and water was kneaded together. When the mixture of powdered graphite and water was loaded into the space 1' as pressure source material, an ultrahigh-pressure experiment was made under the same condition as in the above experiment where only graphite was used as pressure source material. The result is shown in FIG. 6. As seen from the result, ultrahigh pressures in excess of 1 TPa are generated for approximately 0.2 ms because of the disruption of atomic covalent bonds in graphite and hydrogen bonds in water. It is evident on comparing the result in FIG. 5 with that in FIG. 6 that the generation of ultrahigh pressures above 1TPa may originate from the disruption of hydrogen bonds or covalent bonds in a large quantity of water rather than that of covalent bonds in graphite.

Although high temperature of the irradiated part of the pressure source material was not measured in the experiment described above, high temperatures above 4000 K can be considered to be generated because of the disruption of atomic bonds in graphite. It is clear from the result of the experiment that the maximum pressure can be increased to a pressure of 1 TPa or above it with increasing the intensity of the pulsed laser or extending the duration of pulsed laser without changing the peak intensity.

By using the optical system which consists of lens 3*d*1 and objective lens 3*d*2, the spot diameter of pulsed laser beam at the interface between the pressure source material and sapphire anvil is adjusted to the size of the end of pressure source material 2 so that the minimum diameter of the laser beam is not formed within the sapphire anvil 1*a*. Thereby the minimum diameter of the pulsed laser that enables the disruption of atomic bonds in the pressure source material by heating, cannot exist within sapphire anvil 1*a* in which the laser beams passes. Therefore, even if the output power of the laser beam from the pulsed laser equipment 3*a* is increased to some extent, the damage of the sapphire anvil 1*a* due to thermal stress resulting from the local temperature increase can be avoided. Thus as greater pulsed laser can be applied to the pressure source material in the space 1' with longer duration, higher pressure can be generated and these can also be maintained for a longer time.

A simple substance such as graphite having large absorption coefficient and strong atomic bonds, or a compound substance having a large absorption coefficient and strong atomic bonds as a whole, which is a mixture of materials such as graphite, metals, water, etc. having a large adsorption coefficient or strong bonds, can be used as the pressure source material loaded into the space 1' which is formed by a pair of sapphire anvils 1*a*, 1*b* and gasket 1*c*. In order to pack the pressure source material into the space 1' easily, the materials used as pressure source material are crushed into powder.

When the pressure source material has larger absorption coefficient, it can be heated up to higher temperature with smaller light energy because it absorbs the externally supplied light energy with high efficiency. When the pressure source material has stronger atomic bonds, higher pressures can be generated in the space 1' because lager expansive forces can be obtained from the disruption of the atomic bonds.

The pressure source material is constrained in the space partly formed by sapphire anvils 1*a*, 1*b* in which the light energy externally supplied to the pressure source material passes. Sapphire has not only strength enough to sustain the ultrahigh pressure generated in the space but also very high transmittance. Since sapphire does not absorb almost all the light energy passing it, the temperature of sapphire anvil does not rise very much. The sapphire anvil is hard to be damaged due to the passing of light energy. By the way, the following relations is established: $I=I_0 e^{-ad}$ (I: intensity of ejective light, $I_0$: intensity of incident light, a: light absorption coefficient, d: thickness). The light absorption coefficient estimated for a typical type-IA diamond, which can be considered to be favorable with respect to the transmittance, is 6.5 cm$^{-1}$ from the above relation, whereas that for sapphire anvil is 0.28 cm$^{-1}$, which is considerably small compared with type-IA diamonds. Since a large single crystal of synthetic sapphire is available, a larger pressure chamber can be formed with sapphire anvils. Furthermore, sapphire anvils can maintain the pressure source material 2 at high temperature so that heat cannot escape from the pressure source material 2 to the outside, for a considerably long time compared to diamond anvils, because sapphire has much lower thermal conductivity than diamond. Thus, the sapphire anvil is suitable for maintaining ultrahigh pressures generated in the pressure chamber for longer time.

In the embodiment described above, the space 1' in the high-pressure device is formed by sandwiching a metal foil with a hole between opposite sapphire anvils, which has the most simple opposed anvil cell. By the use of anvils more than three, larger pressure chamber can be formed and furthermore the use of the multi-anvil cell enables the irradiation of pulsed laser not only from one direction but also from some different directions. Thereby higher pressures can be expected to be achieved in the large space.

Figure 7:
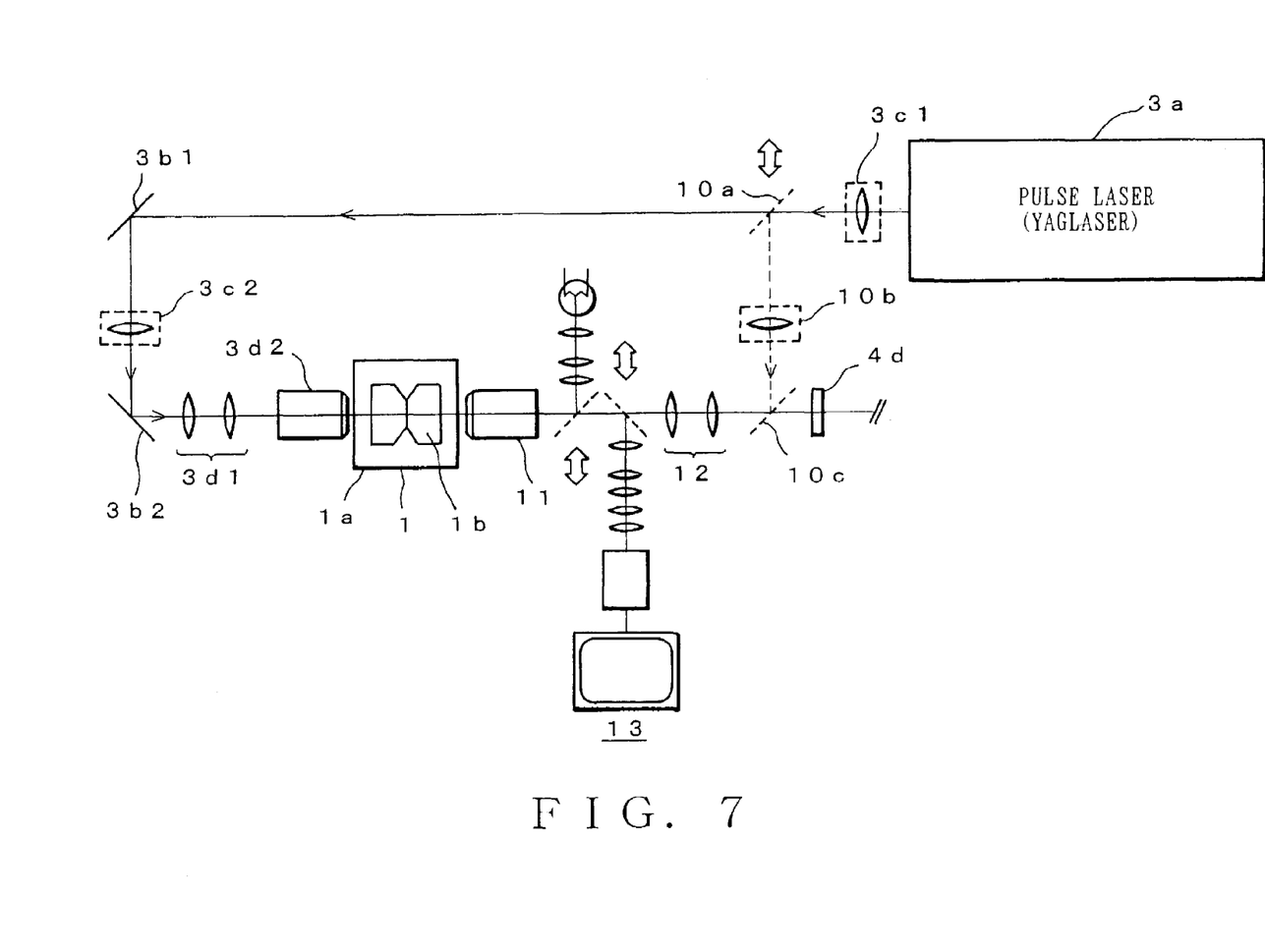
FIG. 7 is a schematic view showing other embodiment of a ultra-high pressure device generating ultrahigh pressures by the use of the present invention.
Figure 8:
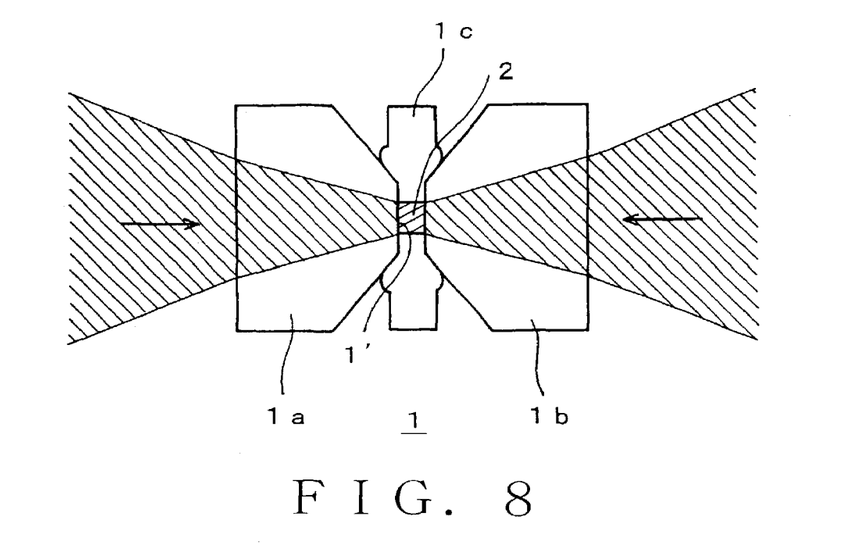
FIG. 8 is a sectional side view showing the high-pressure device 1 in FIG. 7.

A simple device using opposed anvil cells in which pulsed laser lights are applied to the pressure source material through both of two opposed anvils can be proposed as shown in FIG. 7. Here, a laser beam emitted from the pulsed laser equipment 3a is divided into two beams by the beam splitter 10a where one beam goes straight on and another beam is reflected from the beam splitter. The beam which goes straight on is applied to the pressure source material through objective lens 3d2 and sapphire anvil 1a in the same way as that shown in FIG. 1. On the other hand, the reflected beam is led to beam splitter 10c through pupil transfer lens 10b and is reflected from the beam splitter 10c so that it changes its direction at right angles. The reflected beam from 10c is applied to the pressure source material through sapphire anvil 1b. Thus, the light energy is supplied to the space 1' of the high-pressure device 1 from two opposed directions. Therefore, ultrahigh pressures more than two times those in the configuration as shown in FIG. 1 can be achieved in the central portion of the pressure chamber.

In the embodiment as demonstrated in FIG. 7, two same devices to apply pulsed laser to the pressure source material as that in the configuration shown in FIG. 1 are equipped in symmetry on both sides of the sapphire anvil cell 1, where objective lens 11, lens 12, monitor system 13 correspond to 3d2, 3d1, and 3e on the side of sapphire anvil 1a in FIG. 1, respectively.

Two beam splitters in the monitor system 13 are removed from the laser light paths after the position and the size of beam spot are decided using the monitor system 13, in the same manner as in the case of monitor system 3e. When measurements of pressure and temperature are made, lens 11, objective lens 12, and monitor system 13 are removed from the laser light paths together with beam splitters 10a and 10b and subsequently objective lens 4b is returned to the original position.

According to the embodiment described above, the present invention not only enables the generation of ultra-high pressure above 1 TPa but also increases the duration of ultrahigh pressure generation by approximately $10^4$ times compared to the conventional methods. Furthermore, the output of pulsed laser required to generate the ultrahigh pressures is some orders of magnitude less than in the conventional methods. The present high-pressure device can be embodied in considerably small scale compared to the conventional dynamic methods which enable the generation of pressures in the 1-TPa region. In addition, when sapphire anvils are used for constraining expansion of the pressure source material, the pressure chamber having a volume of some cubic millimeters can be established. Thus the ultra-high pressure device based on the present invention has ultrahigh-pressure ability that cannot be achieved by means of any other existing high-pressure methods. The possibilities for discoveries and syntheses of new materials with novel physical and chemical properties are far increased by employing this device. Furthermore, if diamond anvils harder than sapphire are used for volume constraint, ultra-high pressures several orders of magnitude higher than 1 TPa are probably achieved by further development in the present technique.

In the present invention, an ultrahigh-pressure method and the device are proposed, in which a matter constrained by optically transparent materials is disrupted by the irradiation of pulsed laser light through the optically transparent material and ultrahigh pressures above 1 TPa can be achieved by constraining expansion due to the disruption. The duration of the ultrahigh pressure generation is longer by more than four orders of magnitude than those in the high-pressure experiments using laser-driven shock wave which can generate ultrahigh pressures above 1 TPa and is also longer by more than three orders of magnitude than that in the shock wave method using a two-stage gas gun which can generate several hundred gigapascals. The sample volume can be some orders of magnitude larger than those ($10^{-9}$ cm$^3$ at 400-500 GPa) in diamond anvil cells which enable the generation of static ultrahigh pressure. Ultrahigh pressures can be generated by incident laser intensity some orders of magnitude less than in the conventional dynamic methods using high-power pulsed lasers. Thus the present invention provides a means for exploring syntheses of new materials with novel physical and chemical properties and properties of unknown substance which have been impossible of execution until now.

In accordance with the invention, there is provided a method capable of generating ultra-high pressures which have not been achieved so far, in which if only a small light energy enough to heat the pressure source material up to a high temperature required to disrupt its atomic bonds is supplied, ultrahigh pressures can be generated and moreover ultrahigh pressures generated in the volume-constrained space are exceptionally high because extremely large expansive forces occurring from the pressure source material against its very strong bonding forces are extremely large.

In accordance with the invention, there is provided a method of generating ultrahigh pressure, in which since the light energy can be efficiently supplied to the pressure source material and can be well controlled by changing the intensity and the duration of the supplied pulsed laser using the existing pulsed laser equipment which can emit laser lights having a wavelength suitable for heating the pressure source material, the duration of generated ultrahigh pressure can be considerably long compared to the conventional dynamic methods.

In accordance with the invention, there is provided a method for generating ultra-high pressure, in which as the optically transparent material is penetrable to the externally supplied light energy, its temperature hardly rises due to energy absorption and thermal stress hardly occurs. Therefore, the higher pressure can be obtained by applying the larger light energy to the pressure source material.

In accordance with the invention, there is provided a method capable of generating ultrahigh pressure in much lager pressure chamber than in the conventional ultrahigh pressure methods using diamond anvil cells, in which since sapphire has high transmittance compared with diamond and a large single crystal of synthetic sapphire is available at a low price, it is suitable for the material forming the pressure chamber.

In accordance with the invention, there is provided a a method capable of generating controlled ultrahigh pressure according to a sample, in which since the pressure source material is composed of a mixture of materials having large adsorption coefficient or strong bonds which has large absorption coefficient and strong atomic bonds as a whole so that considerably large expansive forces can be obtained even if the supplied energy is relatively small, the peak and the duration of the generated pressure can be controlled by combining materials.

In accordance with the invention, there is provided a method for generating ultra-high pressure that enables the control of temperature in the sample by changing temperature gradients across the pressure source material, in which since the pressure source material can be chosen among materials which have covalent, metallic, and hydrogen bonds according to need, the pressure source material can be adjusted according to the sample by combining materials that have different light absorption coefficients or various thermal conductivities.

In accordance with the invention, there is provided a method for generating ultrahigh pressure with high energy-efficiency by using the pressure source material composed of only graphite.

In accordance with the invention, there is provided a method for generating ultra-high pressure which enables the generation of peak pressure higher than in the case of using graphite singly as the pressure source material.

In accordance with the invention, there is provided a method for generating ultra-high pressure that enables the generation of higher pressure with higher power lasers, in which since the minimum diameter of the laser beam is not formed within the optically transparent material, the most condensed place of the pulsed laser light does not exist in the interior of the optically transparent material, and the local temperature increase in the optically transparent material can be avoided thereby.

In accordance with the invention, there is provided a method for generating ultra-high pressure, that enables the generation of ultrahigh pressure in the lager pressure chamber, with the longer duration, and by some orders of magnitude smaller amounts of energy compared to the conventional methods, in which if only a small light energy enough to heat the pressure source material up to a high temperature required for inducing the disruption of atomic bonds is supplied, ultrahigh pressures can be generated and furthermore ultrahigh pressures generated in the volume-constrained space are exceptionally high because of extremely large expansive forces occurring from the pressure source material disrupted against its very strong bonding forces, and ultrahigh pressures which have not been achieved until now can be generated thereby.

In accordance with the invention, there is provided a device for generating ultra-high pressure that enables the generation of exceptionally high pressure in the space under volume constraint, in which if only a small light energy enough to heat the pressure source material up to a high temperature required for inducing the disruption of its atomic bonds is supplied, ultrahigh pressures can be generated and ultrahigh pressures generated in the volume-constrained space are exceptionally high because of extremely large expanding forces occurring from the pressure source material disrupted against its very strong bonding forces.

In accordance with the invention, there is provided a device for generating ultrahigh pressure with the longer duration compared to the conventional dynamic methods in addition to the effect of the invention in claim 11, in which the light energy can be efficiently supplied to the pressure source material by controlling the intensity and the duration of pulsed laser by using the existing pulsed laser equipment which can emit the laser light having a wavelength suitable for heating the pressure source material.

In accordance with the invention, there is provided a device for generating ultra-high pressures, in which since the minimum diameter of the laser beam is not formed within the optically transparent material, higher-power-pulsed laser can be used for the high-pressure generation without damaging the optically transparent material.

In accordance with the invention, there is provided a device for generating ultra-high pressure in which since larger expansion occurs in the space compared to the irradiation in one direction, higher pressure can be achieved.

In accordance with the invention, there is provided a device for generating ultra-high pressure, which enables the measurement of generated ultrahigh pressures to know how generated pressures are changed by the use of various pressure source materials or by the way of supplying light energy.

In accordance with the invention, there is provided a device for generating ultra-high pressure, which enables the measurement of temperature in the space to know how temperatures in the space during the disruption of atomic bonds in the pressure source material are changed by the use of various pressure source materials or by the way of supplying light energy.

What is claimed is:

1. A method for generating ultra-high pressure comprising the steps of,
   loading a pressure source material, which is a part of a device, under volume constraint in a space partly surrounded by an optically transparent material;
   supplying optical energy to the pressure source material with a pulsed laser beam;
   splitting the pulsed laser beam with an optical splitting means into plural parts to be applied to the pressure source material from plural directions;
   disrupting atomic bonds of the pressure source material by heat of optical energy externally supplied to said pressure source material through said optically transparent material;
   separating atoms of the pressure source material from each other to fly freely under volume constraint;
   expanding said pressure source material under volume constraint through the disruption of the atomic bonds; and
   generating ultra-high pressure within said space using expansive force of said pressure source material arising from the disruption of atomic bonds.

2. The method for generating ultra-high pressure according to claim 1, wherein said optically transparent material has high transmittance to said pulsed laser beam.

3. The method for generating ultra-high pressure according to claim 2, wherein said optically transparent material is sapphire.

4. The method for generating ultra-high pressure according to claim 1, wherein said pressure source material is made of a simple substance having a large absorption coefficient and strong atomic bonds, or a compound substance which is a mixture of materials having the large absorption coefficient andlor the strong atomic bonds to provide the large absorption coefficient and strong atomic bonds as a whole.

5. The method for generating ultra-high pressure according to claim 4, wherein the type of said atomic bonds is a covalent bond, a metallic bond or a hydrogen bond.

6. The method for generating ultra-high pressure according to claim 4, wherein said simple substance is graphite.

7. The method for generating ultra-high pressure according to claim 4, wherein said compound substance is a mixture of powdered graphite and water.

8. The method forge generating ultra-high pressure according to claim 1, wherein said pressure source material is irradiated with the pulsed laser beam through said optically transparent material in such a manner that said pulsed laser beam has a beam spot having a diameter adjusted to that of said pressure source material so that said pulsed laser beam provides a minimum diameter not within said optically transparent material.

9. The method for generating ultra-high pressure according to claim 3, wherein said space is surrounded by optically transparent sapphire anvils.

10. A device for generating ultra-high pressure comprising:
- a pressure source material under volume constraint in a space partly surrounded by an optically transparent material, said pressure source material being expanded in volume through disruption of its atomic bonds; and
- light energy supplying means for externally supplying optical energy to said pressure source material through said optically transparent material, wherein
- said pressure source material is heated by the light energy externally supplied by the light energy supplying means so that said atomic bonds are disrupted, atoms of the pressure source material are separated from each other to fly freely, and ultra-high pressure is generated within said space using expansive force of said pressure source material arising from the disruption of atomic bonds, and wherein
- said light energy supplying means is equipped with a pulsed laser beam, and has an optical splitting means for splitting the pulsed laser beam into plural parts to be applied to said pressure source material constrained in said space from plural directions.

11. The device for generating ultra-high pressure according to claim 10, wherein said light energy supplying means has an optical adjusting system for adjusting the diameter of the pulsed laser beam so that said pulsed laser beam provides a minimum diameter not within said optically transparent material before the pulsed laser beam penetrates said optically transparent material.

12. The device for generating ultra-high pressure according to claim 10, wherein a radiative transition material is loaded together with said high pressure source material in said space, said radiative transition material emitting fluorescence excited by laser and changing its wavelength according to pressure within the space, further comprising:
- a wavelength measuring means for measuring the wavelength of the fluorescence emitted by said radiative transition material; and
- a pressure estimating means for estimating the ultra-high pressure generated within said space from shifts in wavelength of the fluorescence emitted from said radiative transition material.

13. The device for generating ultra-high pressure according to claim 10, further comprising:
- means for measuring the temperatures of said space, wherein spectra of thermal radiations from the space are observed during disruption of said pressure source material and the temperatures are obtained from the observed spectra.

14. A method for generating ultra-high pressure comprising the steps of
- loading a pressure source material, which is a part of a device, under volume constraint in a space partly surrounded by a plurality of optically transparent materials;
- supplying optical energy to the pressure source material from plural directions with a plurality of lasers that emit pulsed beams;
- disrupting atomic bonds of the pressure source material by heat of optical energy externally supplied to said pressure source material through said optically transparent materials;
- separating atoms of the pressure source material from each other to fly freely under volume constraint;
- expanding said pressure source material under volume constraint through the disruption of the atomic bonds; and
- generating ultra-high pressure within said space using expansive force of said pressure source material arising from the disruption of atomic bonds.

15. A device for generating ultra-high pressure comprising
- a pressure source material under volume constraint in a space partly surrounded by a plurality of optically transparent materials, said pressure source material being expanded in volume through disruption of its atomic bonds; and
- light energy supplying means for externally supplying optical energy to said pressure source material through said optically transparent materials, wherein
- said pressure source material is heated by the light energy externally supplied by the light energy supplying means so that said atomic bonds are disrupted, atoms of the pressure source material are separated from each other to fly freely, and ultra-high pressure is generated within said space using expansive force of said pressure source material arising from the disruption of atomic bonds, and wherein
- said light energy supplying means are equipped with a plurality of lasers that emit pulsed beams to be applied to said pressure source material constrained in said space from plural directions.

* * * * *